EA 673 - ST. AUGUSTINEGRASS

Filed Dec. 2, 1969

INVENTORS
JAKE T. GRUIS
EUGENE W. MAYER
JOHN A. LONG

BY

Strauch, Nolan, Neale, Nies & Kurz
ATTORNEYS

United States Patent Office

Plant Pat. 3,180

Patented May 16, 1972

3,180

EA 673—ST. AUGUSTINEGRASS

Jake T. Gruis, Apopka, Fla., and Eugene W. Mayer and John A. Long, Marysville, Ohio, assignors to O. M. Scott & Sons Company, Marysville, Ohio Filed Dec. 2, 1969, Ser. No. 881,640
Int. Cl. A01h 5/00
U.S. Cl. Pl.—88 1 Claim

ABSTRACT OF THE DISCLOSURE

A perennial hybrid St. Augustinegrass having a moderate olive green color, very good gray leafspot resistance and excellent resistance to insects including sod webworms and chinchbugs. This hybrid possesses vigorous growth and is easily propagated.

SUMMARY OF THE VARIETY

This invention relates to a new and distinct perennial St. Augustinegrass selected from a series of hybrids resulting from a cross between a purple stigma male parent (Ea 61108) and a white stigma female parent (Ea 61111). Upon flowering this new hybrid produced florets with purple stigmas. These confirmed the new plant as a hybrid since the purple stigma character was employed as a genetic marker. This hybrid was labeled Ea 673 and propagated vegetatively by stolons to provide planting stock for studying performance and comparison to present commercial varieties.

Ea 673 St. Augustinegrass has very good gray leafspot resistance and excellent insect resistance. In this regard Ea 673 is the only St. Augustinegrass which is resistant to sod webworm attacks, and it can, in part, accordingly be distinguished from other St. Augustinegrasses by this characteristic.

BRIEF DESCRIPTION OF THE ILLUSTRATIONS

DETAILED DESCRIPTION OF THE VARIETY

Figure 3:
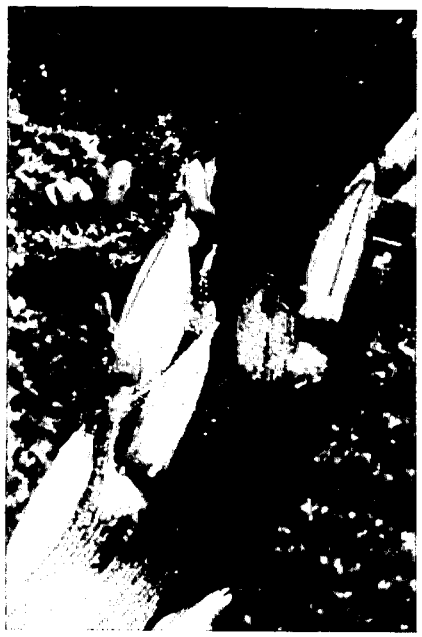
FIG. 3 is a 10× magnification of Ea 673 spikelets showing the purple stigma color and the reduced size of the first glume.
Figure 2:
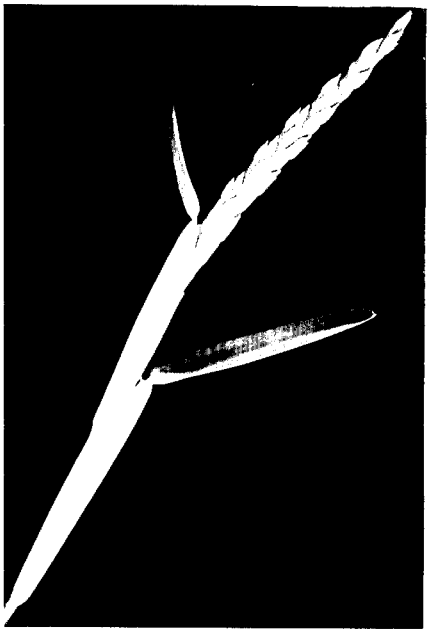
FIG. 2 is a single spike of Ea 673 showing spikelets in groups of two and three.
Figure 1:
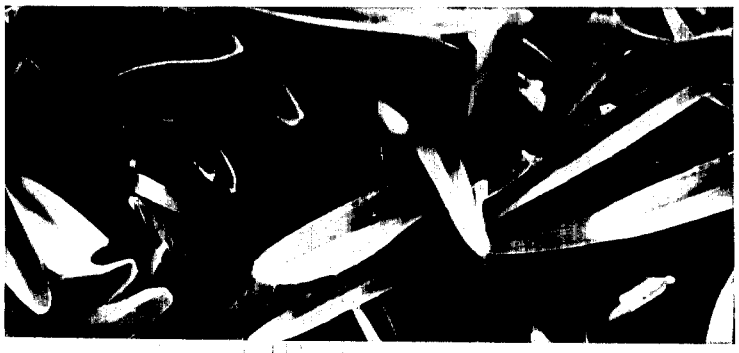
FIG. 1 is a close-up view of Ea 673 turf.

Ea 673 possesses a moderate olive green color (7.5 GY 4/4) [1] and is characterized by compressed and branched

[1] Munsell color designation obtained using a Nickerson color fan. The designated color is of plant material grown in the greenhouse. The color is subject to variation depending upon the environmental conditions under which the grass is grown.

culms with flowering shoots 30–45 cm. tall. The leaf blades average 10 cm. long and over 8.5 mm. wide. Racemes are 8 to 12 cm. long with spikelets solitary, in pairs, and in groups of three. Ea 673 has a purple stigma and an unreduced chromosome number of 18. Ea 673 is easily propagated and possesses vigorous growth characteristics.

The chromosome numbers, stigma colors, and morphological measurements of Ea 673 and other St. Augustinegrasses are compared in Tables 1, 2, and 3 below.

TABLE 1

Chromosome Numbers and Stigma Colors of Ea 673 and Other St. Augustinegrasses

| Selection/variety | Chromosome number (unreduced) [1] | Stigma color |
|---|---|---|
| Ea 673 | 18 | Purple. |
| Ea 611081 | 18 | Do. |
| Floratine | 27 | Do. |
| Bitter Blue | 27 | Do. |
| Texas Common | 18 | White. |

[1] Chromosome number determinations made on pollen mother cells.

TABLE 2

Comparative Leaf Blade Length and Width for Ea 673 and Other St. Augustinegrasses

| Selection/variety | Leaf blade width (mm.) [1] | Leaf blade length (mm.) |
|---|---|---|
| Ea 673 | 7.8–9.6 | 89.7–111.3 |
| Ea 611081 | 7.1–8.5 | 79.3–101.1 |
| Bitter Blue | 7.2–10.2 | 73.6–99.2 |
| Texas Common | 7.7–9.5 | 95.0–129.6 |

[1] Measurements recorded 25 millimeters above leaf collar. All plant material grown unclipped in greenhouse.

TABLE 3

Comparative Morphological Characteristics of Spikelets on Ea 673 and Other St. Augustinegrasses.

| Selection/variety | Length of— First glume (mm.) [1] | Second glume (mm.) | Lemma (mm.) | Palea (mm.) |
|---|---|---|---|---|
| Ea 673 | .91–1.17 | 3.47–3.81 | 3.53–3.99 | 3.33–3.75 |
| Ea 611081 | 1.14–1.52 | 3.79–4.17 | 3.81–4.13 | 3.39–3.71 |
| Bitter Blue | 1.11–1.47 | 4.39–4.77 | 4.13–4.39 | 3.87–4.21 |
| Texas Common | 1.12–1.52 | 3.91–4.53 | 3.87–4.29 | 3.50–3.84 |

[1] Measurements recorded in millimeters using 20× magnification.

While no single one of the foregoing characteristics can be relied upon to distinguish Ea 673 from all other St. Augustinegrasses, taken as a whole they, together with the characteristics of the hairs and barbs on the leaf, readily distinguish this variety from other St. Augustinegrasses as shown by the following table:

TABLE 3a

Composite of Descriptive Characteristics of Ea 673 and Other St. Augustinegrasses

| Characteristic | Ea 673 | Ea 611081 | Bitter Blue | Floratine | Texas Common |
|---|---|---|---|---|---|
| 1. Long hairs on adaxial sheath margin | − | − | − | + | − |
| 2. Barbs on adaxial leaf surface | − | − | + | − | − |
| 3. Hairs on adaxial margin of collar | + | − | ---------- | ---------- | − |
| 4. Numerous hairs on adaxial leaf blade surface | − | − | − | + | − |
| 5. Chromosome number | 18 | 18 | 27 | 27 | 18 |
| 6. Stigma color | (1) | (1) | (1) | (1) | (2) |
| 7. 1st glume | + | + | + | ---------- | + |
| 8. 2d glume | + | + | − | ---------- | − |
| 9. Lemma | + | + | − | ---------- | + |
| 10. Palea | + | + | − | ---------- | + |

[1] Purple. [2] White.

NOTES:

a. In items 1–4, a "+" sign signifies that the characteristic is present and a "−" sign that it is absent. The absence of both signs signifies that the characteristic was not ascertained for the variety.

b. In items 5–10, a "+" sign signifies that the characteristic is not significantly different in comparison to other varieties identified by the same sign. A "−" sign indicates that the characteristic differs in a statistically significant manner. The absence of both signs has the same significance as in items 1–4.

In addition to the foregoing, its growth characteristics and resistance to sod web can also be relied upon to distinguish Ea 673 from other St. Augustinegrasses as is apparent from Tables 4 and 5, which are discussed hereinafter.

Ea 673 has a high degree of hybrid vigor when grown under proper conditions. This vigor, combined with disease and insect resistance it possesses, makes Ea 673 capable of producing a fast growing turf which fills in very rapidly. This vigor is reflected in the amount of clippings removed from test plots as shown by the data in Table 4.

TABLE 4

Fresh Weight of Clippings Removed From Plots of Ea 673 and Other St. Augustinegrasses.

| Selection/variety: | Fresh weights (gms./1.22 m.×1.52 m. plot) |
|---|---|
| Ea 673 | 176.7 |
| Texas Common | 103.7 |
| Ea 611081 | 117.5 |

Ea 673 has a quite acceptable level of tolerance to freezing temperatures. In this regard its cold weather tolerance is much better than that of Floratine and Bitter Blue St. Augustinegrasses as demonstrated by the fall color retention data presented in Table 5.

TABLE 5

Color Retention of Ea 673 and Other St. Augustinegrasses

| Selection/variety | Color [1] | |
|---|---|---|
| | 11/21/68 | 12/20/68 |
| Ea 673 | 10.0 | 6.6 |
| Ea 611081 | 7.0 | 5.6 |
| Bitter Blue | 5.0 | 4.0 |
| Floratine | 2.5 | 3.5 |

[1] Color rating: 10=darkest green, 1=no color retention.

Ea 673 has a high degree of resistance to gray leafspot which continues throughout the entire growing season. Some varieties such as Bitter Blue only show this resistance late in the growing season, and others have little resistance at all to gray leafspot. The superior resistance of Ea 673 to this disease is evident from the data in Table 6.

TABLE 6

Comparative Gray Leafspot Resistance of Ea 673 and Other St. Augustinegrasses

| Selection/variety | Percent Gray Leafspot | | |
|---|---|---|---|
| | 5/6/68 | 10/18/68 | 11/21/68 |
| Ea 673 | 15 | 1 | 0 |
| Bitter Blue | 47 | 35 | 13 |
| Floratine | 47 | 43 | 60 |

One of the most desirable characteristics of Ea 673 is its insect resistance. In areas for which this grass is suitable insects are a constant threat, and the high degree of resistance it possesses enables Ea 673 to survive where grasses such as Bitter Blue, Floratine and Texas Common may be seriously damaged. One of the most troublesome and harmful insects and one to which some other St. Augustinegrasses are very susceptible is the chinchbug. Chinchbug resistance is reflected by the injury caused to the infected plants and also by the actual number infesting an area. Ea 673 attracts very few chinchbugs and is not injured by those which are present as shown by the data in Table 7.

TABLE 7

Comparative Chinchbug Resistance of Ea 673 and Other St. Augustinegrasses

| Selection/variety | Count [1] (1968) | | Injury [2] (1968) | | | | Turf quality (1968) | |
|---|---|---|---|---|---|---|---|---|
| | 9/26 | 12/14 | 9/26 | 10/18 | 11/21 | 12/20 | 10/18 | 11/21 |
| Ea 673 | 4 | 11 | 1.0 | 1.0 | 1.0 | 1.0 | Excellent | Excellent. |
| Ea 611081 | 6 | 60 | 1.0 | 1.3 | 1.0 | 2.0 | do | Good. |
| Bitter Blue | 30 | 65 | 3.6 | 4.0 | 3.3 | 3.3 | Good | Do. |
| Floratine | 75 | 76 | 4.5 | 5.0 | 6.0 | 4.5 | do | Do. |

[1] Actual number per 0.619 square meters.
[2] Injury rating: 1=no injury; 10=severe injury.

Ea 673 also is unique in that it is the only St. Augustinegrass which shows any resistance to the sod webworm. This hybrid sustains only minor damage from sod webworm attacks and maintains a desirable turf while other varieties are severely damaged as demonstrated by the data in Table 8.

TABLE 8

Sod Webworm Resistance of Ea 673 and Other St. Augustine-grasses

| Selection/variety: | Injury [1] |
|---|---|
| Ea 673 | 4.3 |
| Ea 611081 | 7.3 |
| Bitter Blue | 9.3 |

[1] Color rating: 10=darkest green; 1=no color retention.

The data set forth in Tables 5 through 8 were obtained from field tests conducted in Apopka, Florida.

What is claimed and desired to be secured by Letters Patent is:

1. A St. Augustinegrass, substantially as herein illustrated and described.

No references cited.

ROBERT E. BAGWILL, Primary Examiner

UNITED STATES PATENT OFFICE

CERTIFICATE OF CORRECTION

Plant
Patent No. 3,180 Dated May 16, 1972

Inventor(s) Jake T. Gruis, Eugene W. Mayer and John A. Long

It is certified that error appears in the above-identified patent and that said Letters Patent are hereby corrected as shown below:

Column 4, line 50, the footnote should read:

--[1]Injury rating: 1=no injury 10=severe damage--

Signed and sealed this 9th day of January 1973.

(SEAL)
Attest:

EDWARD M.FLETCHER,JR.
Attesting Officer

ROBERT GOTTSCHALK
Commissioner of Patents